(12) United States Patent
Mallon

(10) Patent No.: US 12,336,943 B1
(45) Date of Patent: Jun. 24, 2025

(54) SURGICAL DEVICE AND PATIENT POSITIONING SYSTEM AND METHOD

(71) Applicant: William J. Mallon, Vero Beach, FL (US)

(72) Inventor: William J. Mallon, Vero Beach, FL (US)

(*) Notice: Subject to any disclaimer, the term of this patent is extended or adjusted under 35 U.S.C. 154(b) by 297 days.

(21) Appl. No.: 17/861,160

(22) Filed: Jul. 8, 2022

Related U.S. Application Data

(60) Provisional application No. 63/220,998, filed on Jul. 12, 2021, provisional application No. 63/219,819, filed on Jul. 8, 2021.

(51) Int. Cl.

| | | |
|---|---|---|
| *A61G 7/05* | (2006.01) | |
| *A61B 5/107* | (2006.01) | |
| *A61B 90/60* | (2016.01) | |
| *A61F 9/00* | (2006.01) | |
| *A61G 1/003* | (2006.01) | |
| *A61G 13/06* | (2006.01) | |
| *A61G 13/08* | (2006.01) | |
| *A61G 13/12* | (2006.01) | |
| *A61B 90/00* | (2016.01) | |

(52) U.S. Cl.
CPC .......... *A61G 7/0503* (2013.01); *A61B 5/1072* (2013.01); *A61B 90/60* (2016.02); *A61G 1/003* (2013.01); *A61G 13/06* (2013.01); *A61G 13/08* (2013.01); *A61G 13/121* (2013.01); *A61G 13/124* (2013.01); *A61G 13/1265* (2013.01); *A61B 2090/061* (2016.02); *A61B 2090/067* (2016.02); *A61F 2009/0035* (2013.01)

(58) Field of Classification Search
CPC ...... A61G 7/0503; A61G 1/003; A61G 13/06; A61G 13/08; A61G 13/121; A61G 13/124; A61G 13/1265; A61G 15/00; A61G 13/00; A61B 5/1072; A61B 90/60; A61B 2090/061; A61B 2090/067; A61B 6/04; A61F 2009/0035
See application file for complete search history.

(56) References Cited

FOREIGN PATENT DOCUMENTS

DE 10217219101 B4 * 10/2017 ............. A61G 15/02

* cited by examiner

*Primary Examiner* — Ophelia A Hawthorne
(74) *Attorney, Agent, or Firm* — Lowndes; Stephen C. Thomas

(57) ABSTRACT

A system for reducing the physiologic strain on a surgeon and for reducing turn around time between patient surgical procedures, wherein said surgical procedures are performed successively on patients who are each disposed upon a surgical bed, by providing the ability to repeatably locate and orient surgical assistive features and patient body portions such that surgeon is presented with similar location of surgical assistive features and patient body portions from one surgical procedure to the next. Patient head location may adjusted by inflatable bladders. Patient head rotation, surgeon stool height, operating bed height, wrist rest height and other surgical assistive features are quickly adjustable so as to be repeatable from one surgical procedure to the next. Surgeon fatigue and turn around time between surgical procedures are reduced. The adjustments may be computer-controlled for repeatability and accuracy.

23 Claims, 5 Drawing Sheets

SURGICAL DEVICE AND PATIENT POSITIONING SYSTEM AND METHOD

REFERENCE

This application is a non-provisional of, and claims benefit of priority to, U.S. Provisional Patent Application Ser. No. 63/219,819 entitled SURGICAL DEVICE AND PATIENT POSITIONING SYSTEM AND METHOD, which was filed in the United States Patent and Trademark Office (USPTO) on Jul. 8, 2021, the entire disclosure of which is incorporated herein by reference in its entirety; this application is a also non-provisional of, and claims benefit of priority to, U.S. Provisional Patent Application Ser. No. 63/220,998 entitled SURGICAL DEVICE AND PATIENT POSITIONING SYSTEM AND METHOD, which was filed in the United States Patent and Trademark Office (USPTO) on Jul. 12, 2021, the entire disclosure of which is incorporated herein by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The field of the invention relates generally to systems and methods for locating and positioning patient supporting apparatuses, such as for example headrests, surgical beds or gurneys, and other patient-positioning apparatus' and structures for use in holding a surgical patient's body or body parts in a desired position during a surgical procedure, and for locating and orienting surgical beds, surgeon stools, surgical lighting equipment, surgical operating equipment, operating equipment foot controls, surgeon hand rests, other surgery-related equipment and other surgical assistive devices and elements such that these devices are located and oriented as desired by a surgeon for use during a surgical procedure. A non-limiting example of an application of the system, apparatus, and method of the invention is the positioning and securing of a patient's head, and location and positioning of surgical arm rest(s) and other surgical equipment, during ophthalmologic surgery procedures. The field of the invention further relates to systems and methods for headrests for use in holding surgical patient's head in a desired position during ophthalmologic surgery.

2. Background Art

It has long been understood that reduction of surgeon fatigue, and securely securing a portion of a patient's body that is being operated upon, are important aspects of improving medical outcomes in almost all surgical procedures. Any movement of the patient's body during a surgical procedure, or any awkwardness in the alignment of the patient's body relative to the surgeon's ability to address the surgical site with surgical instruments and equipment, may lead to imprecise execution of the surgical procedure and could result in negative medical outcomes. The result for the patient is a higher probability of negative outcome due to inaccuracies in the surgical procedure caused by an awkward approach required of the surgeon, which leads to increased surgeon fatigue. This is especially true after repeated, successive surgical procedures in a short period of time, for example, within a day. It is desirable to reduce, or eliminate if possible, negative patient outcomes by providing a repeatable, accurate positioning of portions of a patient's body and surgical assistive features.

Further, the present methods for positioning patients and surgical assistive features are performed manually. Differences in patient height, weight, body proportion and other body features requires manual adjustment of gurney height, patient body position features, and other adjustable surgical features between patients. This manual procedure, in addition to being non-repeatable, can be time consuming. Because operating facilities are typically able to bill for use based on procedure, and not on an hourly basis, it is desirable that patient setup time be minimized in order to make more efficient use of the surgical facility.

What is needed in the art is a system and method for positioning and supporting portions of a patient's body, and surgical assistive features such as wrist and hand rests, for a surgical procedure in such a way as to allow the surgeon to accurately and easily address the surgical site; allowing the surgeon to address the surgical site with reduced physical fatigue over the systems of the prior art; and to do so repeatably and quickly between surgical procedures, thus reducing the setup time to prepare a new patient for surgery. This repeatability and reduction setup time would allow for greater efficiency in use of facilities and personnel, reducing costs and increasing effectivity. Importantly, by reducing the physical stress on the surgeon, greater surgical accuracy would be achieved, leading to improved patient outcomes.

BRIEF SUMMARY OF THE INVENTION

The present invention comprises an apparatus, system and method that have one or more of the following features and/or steps, which alone or in any combination may comprise patentable subject matter. The invention may comprise any of the desired features, in any quantity and in any combination. The embodiments described herein are exemplary in nature. The scope of the invention includes the described and depicted exemplary embodiments and all legal equivalents.

The present apparatus, method and system of the invention overcome the shortcomings of the prior art by providing a positioning system for a portion of a patient's body to securely hold portions of a patient's body, and other assistive surgical features such as surgeon hand rests, in predetermined positions during a surgical procedure, said method and system providing, in various embodiments, one or more of the following features and benefits:

Secure positioning of the portion of the patient's body in a predetermined position and orientation such that movement of the patient's body portion during the performing of the surgical procedure is restricted or eliminated;

Accurate positioning and orientation of the patient's body portion, such that certain alignments are achieved, allowing the surgeon to execute operative procedures with increased accuracy and less physical fatigue relative to systems of the prior art;

Repeatable positioning of the patient's body portion such that the positioning and orientation of the patient's body portion is maintained similarly from patient to patient, so that a surgeon operating upon successive patents experiences the same, or very similar, positioning of the patient's body portion from patient to patient when performing successive surgeries; and Repeatable positioning of the assistive surgical features, such as wrist and hand rests, operating equipment foot pedal controls, surgical bed height, surgeon stool height, and other assistive surgical features and elements, such that the positioning and orientation of the assistive surgical features are maintained similarly from patient to patient, so that a surgeon operating upon successive patents experiences the same, or very similar, positioning of the assistive surgical features from patient to patient.

Customizable as between surgeons, so that a particular surgeon's personally preferred parameters may be stored and retrieved, such that the operating theatre is specifically tailored to the operating surgeon;

Automated, controllable adjustment of operating parameters for operating room equipment, by the use of data-networked computers, mobile devices such as cell phones and tablets, and such operating room equipment which may include, for example and not by way of limitation, a surgical bed, a surgeon stool, surgeon hand or wrist support(s), ultrasound equipment, microscope equipment, lighting equipment and camera(s).

In embodiments, the system and method of the invention may comprise one or more of the following features, in any combination: one or more headrests for supporting a patient's head; one or more rests for supporting a patient's neck; an angle measuring device for measuring the rotation of a patient's head; an eye height measuring device for measuring the height of the patient's eye from a reference point; a height measuring instrument for measuring the height of the surgical bed from a reference point (which may, for example, be the ground or floor); a height measuring instrument for measuring the height of the sitting surface of a stool for the surgeon to use during surgical procedures from a reference point (which may, for example, be the ground or floor of the operating theater or room); a height measuring instrument for measuring the height of a reference point of a patient's head (for example, the crown of the patient's eyebrow, or corneal apex or other feature of a patient's eye or facial feature) from another reference point (which may, for example, be the ground or floor, or height of a wrist or hand rest); the height of the wrist-supporting surface of a hand or wrist rest from a reference point such as the supporting surface of a bed or headrest, or corneal apex of a patient's eye; or any combination of the foregoing. In embodiments, the height measuring instruments may be the same instrument or a plurality of instruments.

In embodiments, the headrest may be, but is not necessarily, inflatable, and may comprise one or more inflatable and deflatable bladder sections, wherein each bladder section may be inflatable or deflatable independently of the other bladder section(s) in those embodiments that comprise a plurality of bladder sections. The bladder sections may be in fluid communication with a manual or controllable powered pump such that the bladder may be inflated or deflated. The bladder section(s) may be in fluid communication with a valve so that the bladder section may be deflated.

In embodiments, the height measuring instruments may comprise movable indicators that may be placed at any location along a length of the height measuring instruments and may be securable at a desired location along a length of the height measuring instrument so that they may be adjusted to match the distance from a reference point (which may be the ground or floor of the operating theater or room) to a desired feature such as, for example, bed height, stool height, the height of a portion or features of a patient's body, or patient eye reference point height. In embodiments, the movable indicators may be slidably engaged with the height measuring instrument so as to be slidable along the length of the height measuring instruments, and secured in a desired location indicating a distance representing the height of a desired feature above the reference point. The movable indicators may be marked with indicia so as to identify the desired feature.

In embodiments, the system and method of the invention may comprise a mat or other floor covering for locating surgical instrument fool pedal controls relative to one another or relative to a reference point, and the location of a surgical bed in a desired location and relationship that is preferred by a specific surgeon. In embodiments, each surgeon using an operating theater may have their own mat, or their own set of positioning markings on a mat, identified to them via markings on the mat such as marking with the surgeon's name or other identifier, each mat or each set of markings identifying that surgeon's preferred placement and arrangement of foot pedal controls, stool location, bed location, and location of other equipment or apparatuses. These markings allow operating room staff to quickly reposition pedal controls, stool location, bed location, and location of other equipment or apparatuses to a surgeon's preference prior to the surgeon entering the operating room, enabling the surgeon to immediately or at least very quickly begin the operating procedure. This reduces total operating time, increases operating room efficiency, and allows an increased number of surgical procedures to be performed in a given period of time, because each surgeon entering the operating room does not need to spend time rearranging pedal controls, stool location, bed location, and location of other equipment or apparatuses to their personal desired location and configuration.

In embodiments, the system and method of the invention may comprise a height-adjustable hand or wrist rest, that may, in embodiments, be controllable by a computer or controller as to its position adjustment, that may be adjusted to a specified distance from a reference point and secured in that position such that the hand or wrist rest is secured, or locked, into a specific defined location that is selected to as to reduce stress or strain on the physicians wrist, or hand, or both, or to improve surgical accuracy, during surgery.

In embodiments, the invention may comprise a method for reducing the physiologic strain on a surgeon and for reducing turn-around time between patient surgical procedures, wherein said surgical procedures are performed successively on patients who are each disposed upon a surgical bed, by providing the ability to repeatably locate and orient surgical assistive features and patient body portions such that a surgeon is presented with similar location and orientation of surgical assistive features and patient body portions from one surgical procedure to the next, comprising: providing a system comprising one or more headrests for supporting a patient's head, wherein a height of said headrest above a reference point of the surgical bed is adjustable; one or more rests for supporting a patient's neck; an angle measuring device for measuring the angle of rotation of a patient's head; an eye height measuring device for measuring the height of the patient's eye from a first reference point; a surgical bed height measuring instrument for measuring the height of the reference point of the surgical bed from a second reference point (which may, for example, be the ground or floor); a stool height measuring instrument for measuring the height of a sitting surface of a stool for the surgeon to sit upon during surgical procedures from said second reference point (which may, for example, be the ground or floor); and a head height measuring instrument for measuring the height of a reference point of a patient's head (for example, the crown of the patient's eyebrow) from said second reference point (which may, for example, be the ground or floor).

The method of the invention may further comprise the steps of adjusting the patient's head height to a pre-determined height above the reference point of the surgical bed by adjusting the height of the headrest; adjusting said patient's head rotation by rotating said patient's head while said patient's head is disposed upon the headrest until the rotation of said patient's head reaches a desired rotation, or angle α (see FIG. 2), as measured by the angle measuring device; securing the patient's head so that it cannot move or rotate during surgery, adjusting a height of said surgical bed until said surgical bed height reaches a desired height from said second reference point as measured by said surgical bed height measuring instrument; and adjusting a height of a stool until the stool sitting surface reaches a desired height from said second reference point as measured by the stool height measuring instrument.

In embodiments, the headrest may comprise one or more inflatable bladders for supporting a patient's head, and wherein the height of said patient's head from said second reference point may be adjusted up or down by inflating or deflating said one or more inflatable bladders. The one or more bladders may be pneumatically inflatable, and may be in fluid communication with an air pump for inflating said one or more bladders. In embodiments, the air pump is manually operated or may be controllable and electrically operated. The one or more inflatable bladders may be in fluid communication with a valve adapted to allow a fluid within the one or more inflatable bladders to escape, thus deflating the one or more inflatable bladders.

The method may further comprise the step of placing a floor mat in a desired location on the ground or a floor, wherein the floor has marking for locating at least one surgical instrument foot pedal control, wherein the location of the at least one surgical instrument foot pedal control is determined by surgeon preference. Additionally the floor may be large enough that the surgical bed rests upon it, and the mat may contain markings for locating the wheels of the surgical bed such that it is in a specified, desired relationship to the foot pedal controls.

The following are objects of the system and method of the invention:
- Reduce turn-around time between patient surgical procedures, thereby enabling more efficient use of operating room and enabling an increased number of procedures to be performed in a given amount of time;
- Provide repeatably adjustable surgery bed height;
- Provide repeatably adjustable patient height;
- Provide repeatably adjustable surgical stool height;
- Provide repeatably adjustable tilt angle of a patient's body portion for surgery;
- Reduce physiologic strain on a surgeon after repeated surgical procedures, thus reducing surgeon fatigue; and
- Improve patient outcomes by providing a more repeatable and consistent surgical operating environment from procedure to procedure.

The features and elements of the invention described and depicted in the accompanying figures may be present in any number, and in any combination, in the various embodiments of the invention.

While the system and method of the invention is useful for any surgical operating room or theater without regard to the specific type of surgery performed there, without limiting the general applicability of the system and method of the invention to any type of surgery, it is noted that an exemplary use case is the use of the system and method of the invention is for ophthalmologic surgery such as, for example, surgery to remove cataracts from a patient's eye.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating exemplary embodiments of the invention and are not to be construed as limiting the invention. In the drawings.

DETAILED DESCRIPTION OF THE INVENTION

The following documentation provides a detailed description of the invention.

Although a detailed description as provided in this application contains many specifics for the purposes of illustration, anyone of ordinary skill in the art will appreciate that many variations and alterations to the following details are within the scope of the invention. Accordingly, the following preferred embodiments of the invention are set forth without any loss of generality to, and without imposing limitations upon, the claimed invention. Thus the scope of the invention should be determined by the appended claims and their legal equivalents, and not merely by the preferred examples or embodiments given.

As used herein, "assistive surgical features" includes within its meaning any feature that assists in the position and/or orienting of any feature or structure that secures, positions, locates, or orients, for example and not by limitation, one or more of the following during a surgical procedure: a portion of a patient's body; a surgical lamp or light element; a surgical hand or wrist rest; a camera for taking video or photographs of the surgery, surgical sight, or portion of a patient's body; and the location of a foot control for an element of equipment used during a surgical procedure.

As used herein, "fluid" includes within its meaning both gases, such as air, and liquids. Thus, an inflatable bladder may be in fluid communication with a pump for filling the bladder with either liquid or gas, such as air. In non-limiting embodiments, the fluid pumps and inflatable bladders of the system of the invention utilize air.

Figure 1:
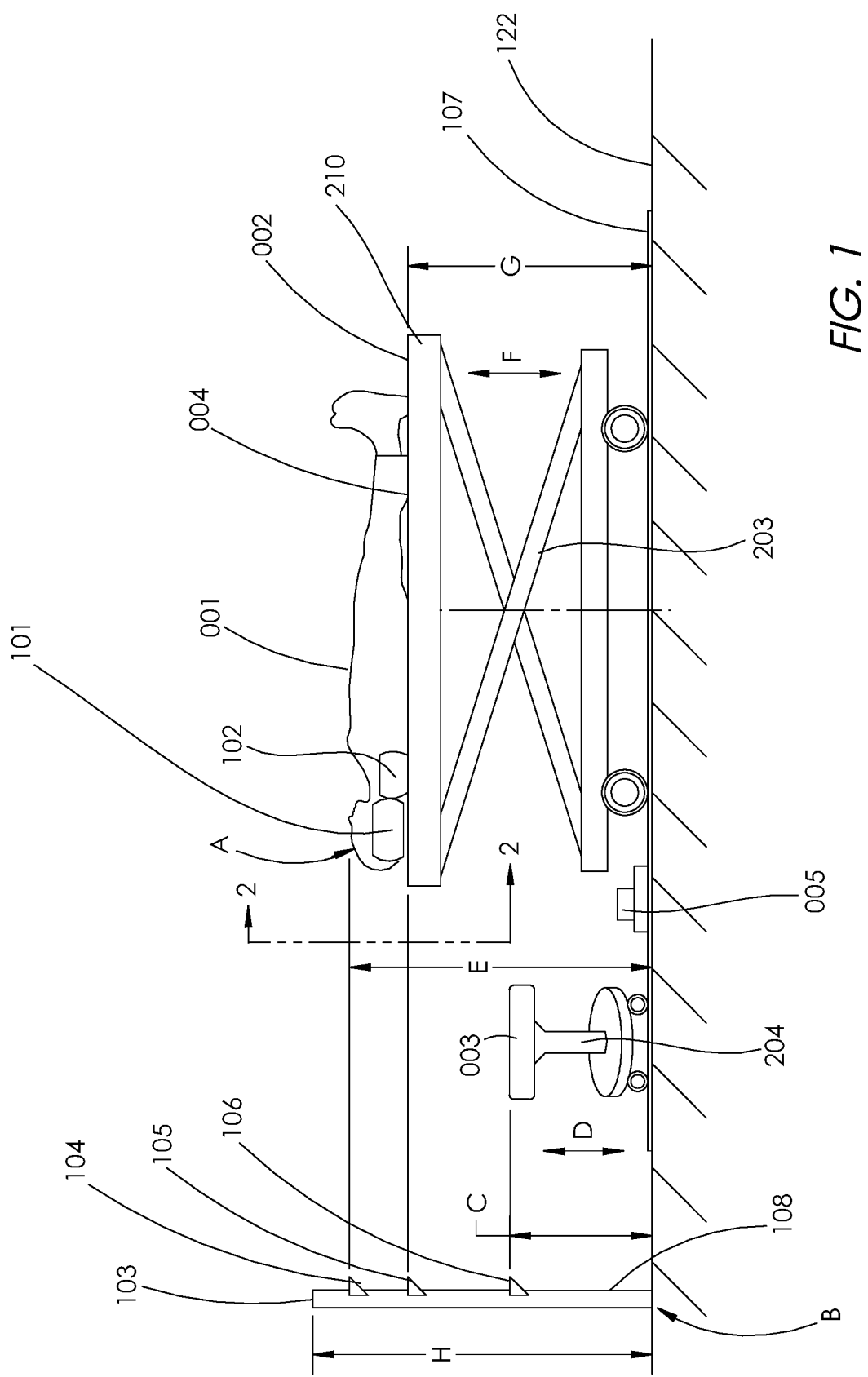
FIG. 1 depicts a side view of an exemplary embodiment of the system of the invention as may be used in a typical operating room. The arrangement of elements depicted in the figure is but one of any number of arrangements comprising the embodiments of the invention. The arrangement of elements may be determined by surgeon preference, which may differ among surgeons.

Referring now to FIG. 1, an exemplary embodiment of the system of the invention is depicted. It is to be understood that the embodiment depicted in is illustrative of but one of any number of arrangements of the system. Generally, the location and orientation of the elements of the system, the surgical assistive features, and the patient's body portions will be determined by surgeon preferences. The arrangement of elements and features depicted in FIG. 1 is merely illustrative and is not to be taken as limiting.

Still referring to FIG. 1, a surgical patient 001 is disposed upon surgical bed 002, which is adjustable in the direction indicated by F so that bed resting surface 004 may be adjusted, e.g., lowered or raised, to achieve a pre-determined height G above ground or floor surface 122. Surgical bed 002 may comprise features that enable patient resting surface 004 to be positioned at any desired height G as determined by the height of the surgeon, the physical attributes of the patient, the desired height of a specific body portion of the patient, surgeon preferences, and so on. Surgeon stool 003, which may be used by the surgeon as support for sitting during surgery, may also be adjustable in the direction indicated by D so that it may be adjusted to predetermined height C from ground or floor surface 122 as desired by the surgeon. Height D may be established, for example, by surgeon preference.

Still referring to FIG. 1, a patient reference point A on surgical patient 001 may be any feature of a portion of patient 001's body, for example, the crown of an eyebrow or corneal apex of the patient's eye. The height E of reference point A from ground or floor surface 122 may be adjusted to a pre-determined value by use of headrest 101 as discussed below. Neck rest 102 may be constructed of any pliable or compressible material, but in embodiments may comprise one or more inflatable bladders. In embodiments, the one or more inflatable bladders of neck rest 102 may be in fluid communication with fluid pump 206 (see FIG. 5), which may be an air pump, or air valve, for inflating and/or deflating the one or more inflatable bladders of neck rest 102. In embodiments, the fluid pump may be manually operated, and may be a hand-operated bulb type manual air pump, or it may be an electronically controllable electrically operated fluid pump 206 that is in communication with a controller such as controller 1001 for controlling the pump action of fluid pump 206 to inflate or deflate neck rest 102.

Still referring to FIG. 1, headrest 101 may comprise one or more inflatable bladders that are in fluid communication with a fluid pump 209 (see FIG. 5), that may be an air pump, or air valve, via tubing 110 (not shown in FIG. 1, but shown in FIG. 2) for inflating and/or deflating the inflatable bladder of headrest 101. In embodiments, the fluid pump 209 may be manually operated, and may be a hand-operated bulb type manual air pump as depicted as item 109 (not shown in FIG. 1, but shown in FIG. 2), or it may be an electronically controllable electrically operated fluid pump 209 that is in communication with controller 1001 (see FIG. 5) for inflating or deflating the bladder(s) of headrest 101. The one or more inflatable bladders comprising headrest 101 may also be in fluid communication with a valve 130 (not shown in FIG. 1, but shown in FIG. 2) for deflating the one or more inflatable bladders comprising headrest 101. By inflating or deflating the one or more inflatable bladders comprising headrest 101, the height E of a patient's body portion, which may be, for example, the crown of a patient's eye brow or the patient's corneal apex, may be adjusted to be located at a predetermined, desired height E from ground or floor surface 122. Height E may be established, for example, by surgeon preference.

Still referring to FIG. 1, the measuring and adjusting of heights of point A (patient body portion), C (surgeon stool), G (surgical bed height), and wrist rest surface 200 (see FIG. 4) from a second reference point such as, for example, ground or floor surface 122, may be aided by a measuring device 103, which, in embodiments, may be an elongate structure having a height H, and a track or other feature 108, which may, in embodiments, run along one edge of elongated structure 103 for allowing sliding adjustment and securing of first marker 104, second marker 105 and third marker 106 at any point along the length of track 108 as determined the method steps of the invention. In use, first marker 104 may be slidingly engaged with track 108 and may be adjusted to be located along track 108 of measuring device 103 at a point that is located a distance E from the bottom end B of measuring device 103; second marker 105 may be slidingly engaged with track 108 and may be adjusted to be located along track 108 of measuring device 103 at a point that is located a distance G from the bottom end B of measuring device 103; and third marker 106 may be slidingly engaged with track 108 and may be adjusted to be located along track 108 of measuring device 103 at a point that is located a distance C from the bottom end B of measuring device 103. A fourth movable marker may be slidingly engaged with track 108 and may be used to identify a desired height of wrist rest surface 200 from the floor or ground 122. Any number of markers may be slidingly engaged with track 108 of measuring device 103, providing an ability to locate any number of features of the body of a patient, equipment, or apparatuses.

In embodiments, markers 104, 105, 106 and any other markers used in similar fashion may be lasers that project a beam horizontally to reference point on the body portions of a patient or surgical equipment or apparatuses, providing a visual mark for a predetermined height of such patient body portions, equipment or apparatuses, such that the height of such patient body portions, equipment or apparatuses can be adjusted relative to a reference such as the ground or floor of the operating room.

In embodiments, measuring device 103 may be embodied as a plurality of separate height indicating devices: a surgical bed height measuring instrument for measuring the height of the reference point of the surgical bed from a second reference point (which may, for example, be the ground or floor); a stool height measuring instrument for measuring the height of a sitting surface of a stool for the surgeon to sit upon during surgical procedures from the second reference point (which may, for example, be the ground or floor); and a head height measuring instrument for measuring the height of a reference point of a patient's head (for example, the crown of the patient's eyebrow or corneal apex) from the second reference point (which may, for example, be the ground or floor).

In any of the embodiments of the invention, the heights of the body portions of a patient, or the height of any surgical assistive feature, equipment or apparatus, such as the surgical bed, foot pedals, stool, lighting, camera and other equipment relative to each other may be predetermined by a surgeon as is most favorable to them personally. The height values may then be saved or recorded by any known means, for example by recording in an operating room notebook, allowing operating room staff to adjust such heights prior to the surgeon entering the operating room, increasing operating room efficiency by greatly reducing or eliminating the time required for a surgeon to re-position and adjust the height of such features after they enter the surgical theater. Using the system of the invention, the surgical theater staff may adjust the height of surgical assistive features, equipment or apparatuses prior to the surgeon's entry into the surgical theater so that the surgeon may enter the theater and begin surgery more quickly.

Still referring to FIG. 1, in embodiments, the system of the invention may comprise a floor mat 107 for locating at one or more surgical instrument foot pedal controls, surgical lamp controls, or other foot controls 005. The location of the at least one surgical instrument foot pedal control 005 on floor mat 107 may be determined by surgeon preference.

Figure 2:
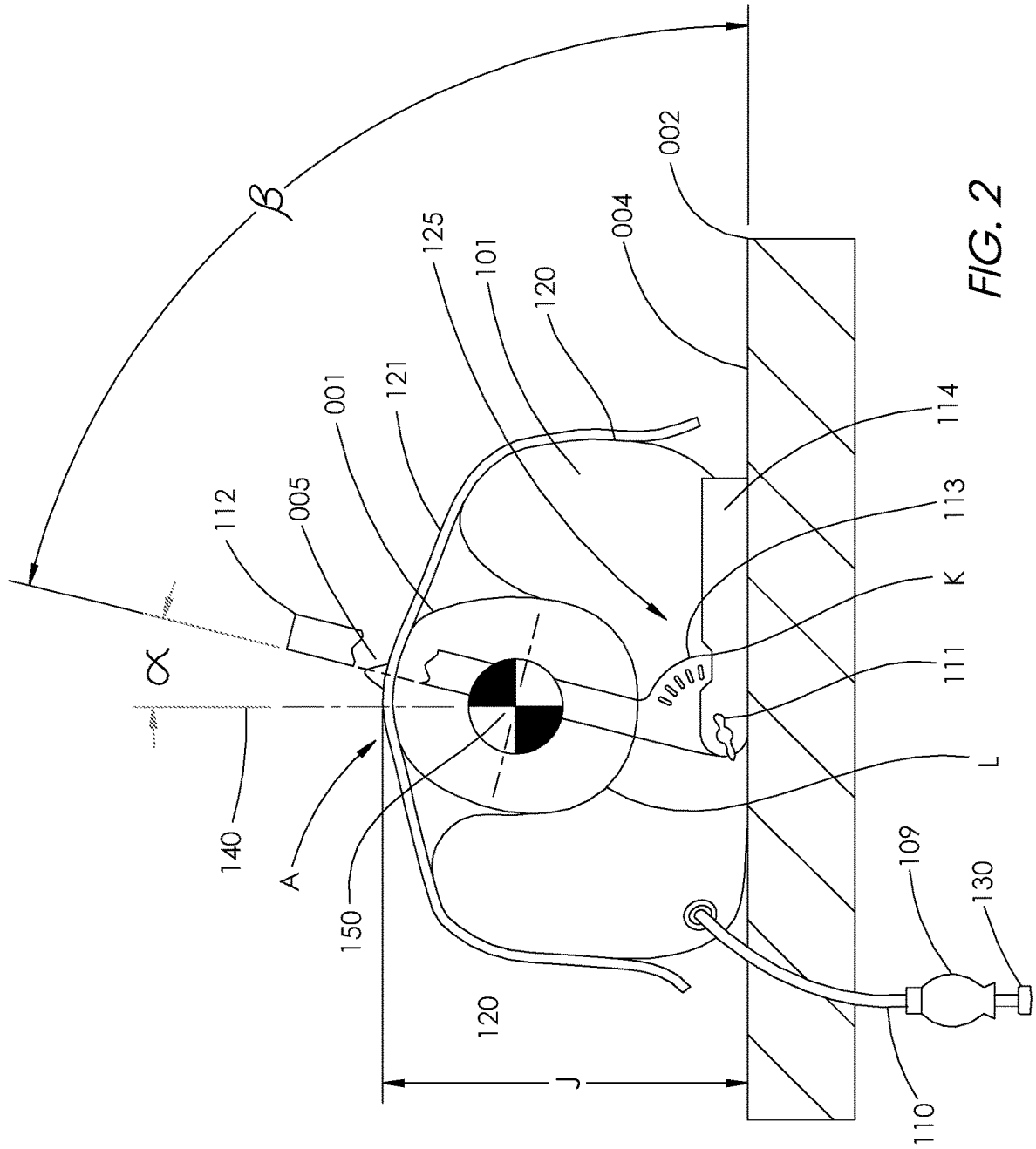
FIG. 2 depicts a view of the surgical patient's head in the headrest of the invention as viewed from the "head end" of the surgical bed, and shows an angle α that measures the rotation, or tilt, of the patient's head from normal, where "normal" is defined as a vertical line, i.e., a line that runs parallel to the force of gravity.

Referring now to FIG. 2, a view from the head end of a surgical bed 002 is depicted. Patient 001 is generally disposed on resting surface 004 of surgical bed 002. It may desired for certain surgical procedures that a portion of a patient's body, such as the patient's head as depicted in FIG. 2, be placed at an angle α from a vertical reference line 140, where a vertical reference line 140 is a line that runs parallel to the force of gravity (i.e., perpendicular to the horizon line, which runs perpendicular to the force of gravity), and runs through reference point 150 which may be a center point of the top of patient 001's head. The patient 001's head or other body portion may be secured in place so that there is no movement or rotation of the head or other body portion of patient 001 during a surgical procedure, by one or more straps 121 that may be secured to the headrest 101 by releasable hook and loop or other fasteners 120.

Still referring to FIG. 2, headrest 101 may comprise one or more inflatable bladders that are in fluid communication with an air pump or air valve via tubing 110 for inflating or deflating the inflatable bladder of headrest 101, or both. In embodiments, the air pump may be manually operated, and, further, in embodiments may be a hand-operated bulb type manual air pump as depicted as item 109. The one or more inflatable bladders comprising headrest 101 may also be in fluid communication with a valve 130 for deflating the one or more inflatable bladders comprising headrest 101. By inflating or deflating the one or more inflatable bladders comprising headrest 101, the height J of a patient's body portion A from a first reference point, such as surgical bed surface 004, may be measured by markings on angle measuring device 125, or by a ruler or other distance-measuring device. Reference point A may be, for example, the crown of a patient's eyebrow or the corneal apex of the patient's eye. Reference point A may be adjusted to be located at a predetermined, desired height E from ground or floor surface 122. Height J may be predetermined, for example, by surgeon preference.

Still referring to FIG. 2, the system of the invention may comprise angle measuring device 125. Angle measuring device 125 may comprise a base leg 114 and an angle measuring leg 112 that are pivotably, or rotatably, connected at point 111. The pivotal or rotating connection between base leg 114 and angle measuring leg 112 may be any pivotal or rotating connection as is known in the mechanical arts but may be, for example, a threaded fastener located at point 111 that may be loosened to allow base leg 114 and angle measuring leg 112 to pivot or rotate relative to one another, and may be tightened to prevent base leg 114 and angle measuring leg 112 from pivoting or rotating relative to one another. Thus, angle measuring device 125 may be adjusted so as to define angle β, which is a measure of the tilt, or rotation, of the patient's head from the plane defined by the surface 004 of surgical bed 002. In embodiments, angle α=180°−angle β. Angle measuring device 125 may comprise markings 113 for viewing relative to reference surface or marking K on angle measuring device 125. While a specific structure is depicted in FIG. 2, any structure suitable to determine angle β may comprise the invention.

Still referring to FIG. 2, once heights C, J, E, R and G, or as many of them as desired by the surgeon, and once the patient 001's head tilt, or rotation, has been adjusted to predetermined values for α, β, and/or γ (see FIG. 3), the patient's head may be secured by one or more releasable, adjustable straps 121 such that it is prevented from moving or rotating during surgery.

Figure 3:
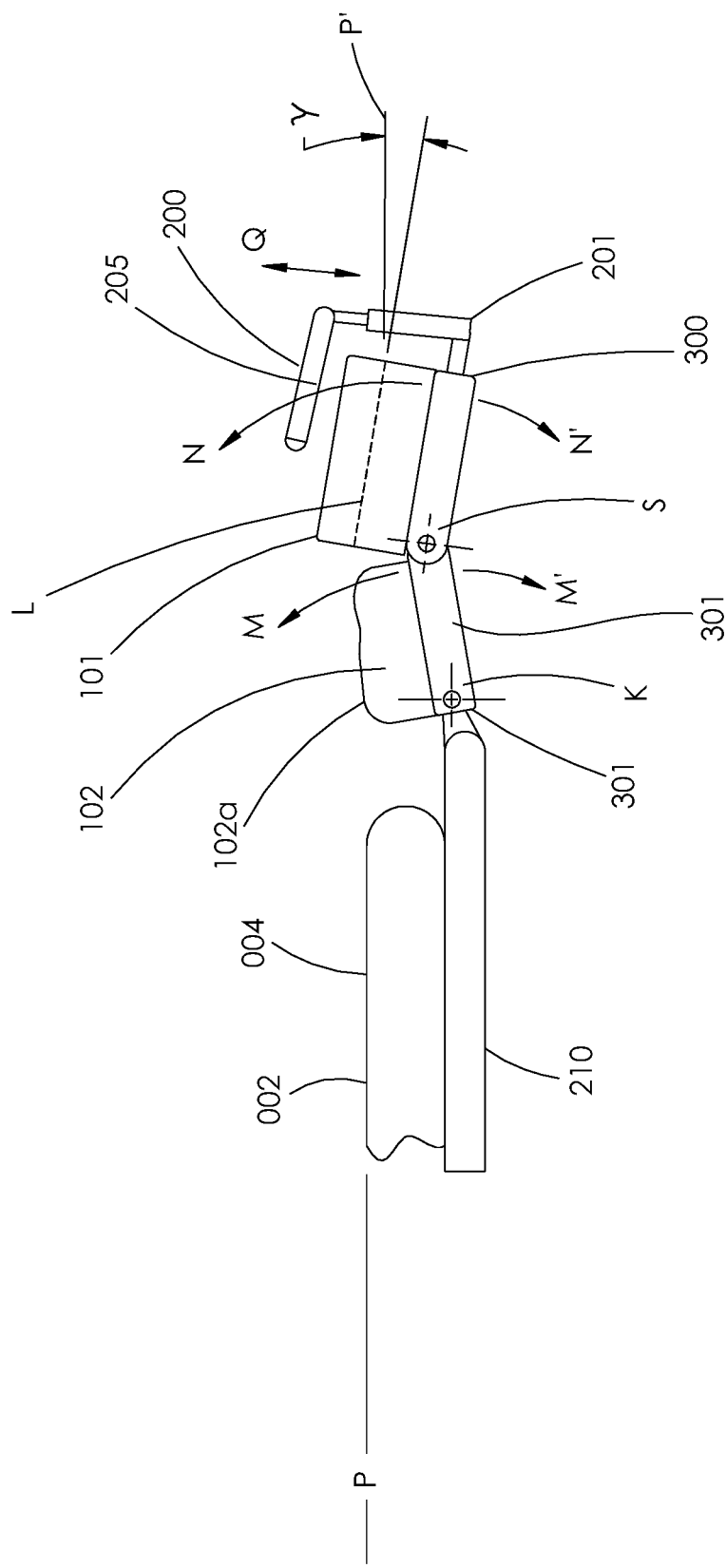
FIG. 3 depicts a side view of a portion of an exemplary head rest portion of the system of the invention, showing the adjustable hand or wrist rest.
Figure 4:
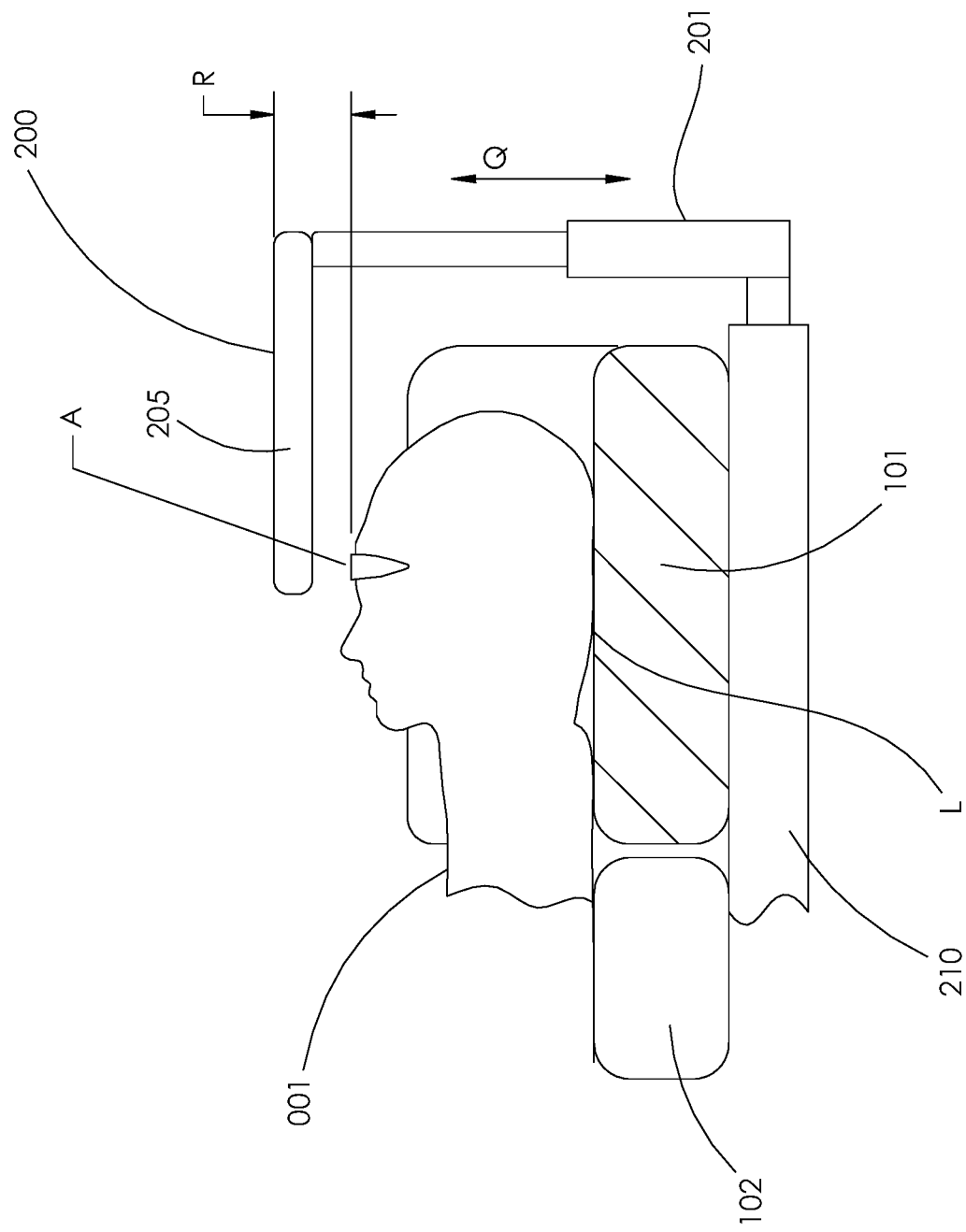
FIG. 4 depicts a side view of a portion of an exemplary head rest portion of the system of the invention, showing the controllable adjustable hand or wrist rest, and showing a patient's head supported by the controllable head rest of the invention and depicting the parameters for determining the height of the wrist supporting surface 200 of hand or wrist rest 205.

Referring now to FIGS. 3 and 4, an exemplary embodiment of the headrest portion of the system of the invention is depicted. Surgical bed 002 that has a patient resting surface 004 in a plane P may be supported by a bed frame 200, which may be, for example, a portion of a gurney or stretcher. Head rest supports 300 and 301 may be pivotably attached at points K and S, allowing them to rotate in the directions N, N' and M, M', respectively, for the purposes of allowing adjustment of the location and tilt angle γ of a patient's head. Headrest 101, having a head resting surface L, may be attached to a surface of support 300 by any means such as, for example, hook and loop fasteners. Likewise optional neck rest 102, having a patient neck-resting surface 102a, may be attached to a surface of support 301 by any means such as, for example, hook and loop fasteners. Headrest 101 and neck rest 102 may comprise inflatable bladders that may be inflatable and deflatable manually or by controllable fluid pump 205 and 206, respectively, which may, for example, be an air pump, for controlling the height of head rest surface L and neck rest surface 102a as herein described. The rotation of supports 300 and 301 at pivotal attachment points K and S may be manual, for exampling using friction from loosening and then tightening threaded fasteners to adjust and then hold supports 300 and 301 in place, or may be controllable and adjustable using controllable rotary motors, actuators or encoders 208 (see FIG. 5), or similar structures as are known in the art for controllable rotation of a structure, for rotating supports 300 and 301 and holding them in place, to achieve a desired angle γ between a reference plane P' that is parallel to plane P, and head resting surface L. The system of the invention may further comprise a wrist rest or hand rest 205 for use by the surgeon, which may have a hand or wrist resting surface 200. The wrist rest 205 may comprise a controllable actuator 201 for adjusting a height of wrist resting surface 200 from the corneal apex, or other patient feature, A, to a surgeon-referred desired height R as depicted in FIG. 4 by causing the hand or wrist rest 205 to be motivated in the direction of arrow Q.

In embodiments, the surgeon stool 003, surgical bed 002, and hand or wrist rest 205 may comprise controllable actuators for raising and lowering the surgeon stool 003 and/or surgical bed 002 to a desired height C and/or G, respectively, and for adjusting an adjustable surgeon hand rest 205 to a desired position and orientation, such as height R from a patient's corneal apex A as shown in FIG. 4.

Figure 5:
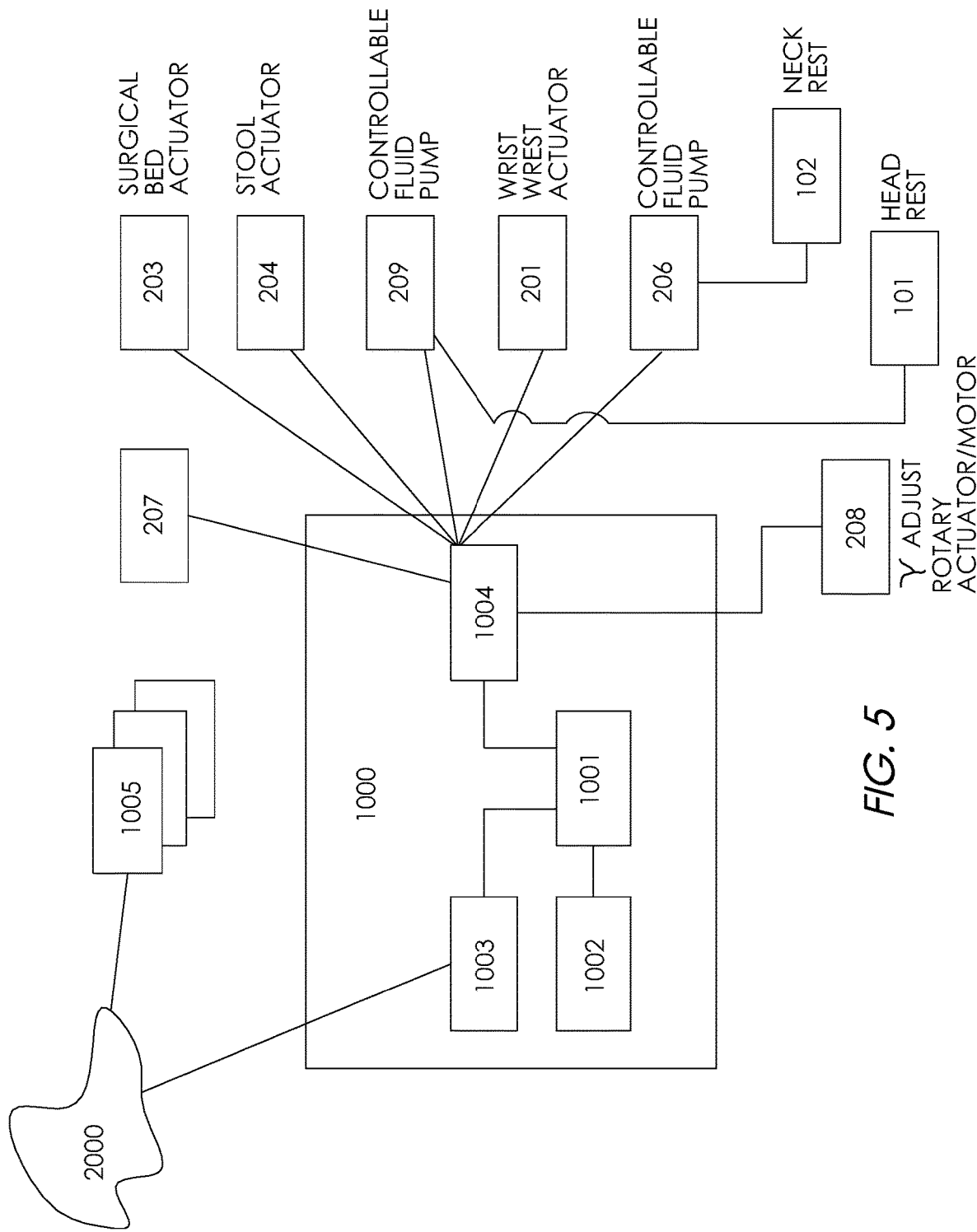
FIG. 5 depicts a block diagram of an exemplary system of the invention.

Referring now to FIG. 5, a block diagram of an exemplary system of the invention is depicted. The system may comprise a local computer 1000, which may be any computer or electronic device that is operable as follows. Local computer 1000 may comprise a physical computer readable media 1002 for storing non-transitory computer readable and executable instructions (software) that are retrieved by controller 1001 to carry out functions of the invention. Controller 1001 may be in communication with one or more input devices such as, for example, keyboard, touchscreens, or microphones, for receiving input data into controller 1001. Likewise, controller 1001 may be in communication with one or more out devices such as, for example, speakers or visual displays for providing output to a user. Media 1002 may be in communication with controller 1001 that is capable of reading and executing the non-transitory computer readable and executable instructions stored on media 1002 and for retrieving predetermined parameters for, for example, height of surgical bed from floor G, height of stool sitting surface from floor C, height of portion of patient's body (such as for example, corneal apex) from floor E, distance from of portion of patient's body (such as for example, corneal apex) from patient resting surface of surgical bed J, angle of rotation of patient's head $\alpha$, angle of headrest $\gamma$. Controller 1001 may also be in communication with at least one transceiver 1004 that is in wired or wireless communication with one or more controllable elements of the system, including surgical bed actuator 203 for controlling the height of the resting surface of surgical bed 002, surgeon stool actuator 204 for controlling the sitting surface of surgeon stool 003, a first controllable fluid pump 209 for inflating or deflating bladders that comprise head rest 101, a second controllable fluid pump 206 for inflating or deflating bladders that comprise neck rest 102, wrist rest actuator 201 for controlling the position or height of wrist rest surface 200, and surgical equipment 207. Controller 1001 may also be in communication with one or more transceivers 1003 for communicating through data network 2000, which may be, for example and not by way of limitation, any data network such as a Local Area Network (LAN), Wide Area Network (WAN) or any other network, and may include connection to the Internet or world wide web 2000, such that controller 1001 is in communication with one or more network-connected mobile devices, electronic devices or computers 1005 such that the mobile devices, electronic devices or computers are operable to communicate with controller 1001. Thus, a user of the system may input one or more parameters for controlling the controllable devices of the system into one of the network-connected mobile devices, electronic devices or computers 1005, whereupon the entered parameters are communicated to controller 1001. Controller 1001 may then communicate the parameters to the controllable devices of the system, causing them to adjust, for example, to a specific surgeon's settings for the next surgery in the operating theatre.

Still referring to FIG. 5, the controllable actuators of the controllable devices of the invention may be any controllable actuator such as, but not limited to, electrical actuators, pneumatic actuators, or hydraulic actuators, and they may be in data communication, wirelessly or wired, with a local computer 1000 through one or more wired or wireless transceiver(s) 1004. Further, the inflatable bladders of headrest 101 and neck rest 102 may be in fluid communication with controllable fluid pumps 209 and 206, respectively, that may also be in data communication, wirelessly or wired, with local computer 1000. Controllable fluid pumps 209 and 206 may be operable to inflate or deflate, or both, the inflatable bladers that comprise head rest 101 and neck rest 102. In embodiments, a user may enter parameters for heights C, G, J, and R and other desired parameters, such as $\alpha$, $\beta$, or $\gamma$ into local computer 1000, or into a remote mobile device or computer 1005 in communication with local computer 1000, either wirelessly or wired. Such remote mobile devices or computers 1005 may execute non-transitory computer readable and executable instructions ("software") for carrying out the functions of communicating the desired heights C, G, J and R and other desired parameters, such as $\alpha$, $\beta$, or $\gamma$, to local computer 1000. In turn, local computer 1000 may then execute software for communicating each parameter to its associated device comprising a controllable actuator or fluid pump, for example, height parameter C to surgeon stool 003, height parameter to surgical bed 002, etc. In response, the controllable actuator of each associated device may then adjust that device to the desired parameter value that was entered by the user; for example, the controllable actuator of surgeon stool 003 may adjust its height to the value of C parameter entered by the user, the controllable actuator of surgical bed 002 may adjust its height to the value of G parameter entered by the user, and so on. The parameters may be stored in physical storage media located in local computer 1000 or in physical storage media located in one or more of the local devices that are in data communication with local computer 1000. These parameters may be saved and stored such that they are identifiable to a particular surgeon. Each surgeon may store their own unique set of parameters. Thus, it may be possible, by the inputting of one or only a few commands into a remote device 1005 or local computer 1000, to command local computer 1000 to communicate the parameters desired by a particular surgeon to each associated controllable device such as surgical bed actuator 203, surgeon stool actuator 204, wrist rest actuator 201, or controllable fluid pumps 205 and 205, or surgical equipment 207 which may include, for example, a controllable microscope, a controllable ultrasound, or a controllable lamp; and, in response, these controllable devices may the adjust automatically to the desired entered parameter values that have been communicated to them. The time required to adjust the surgeon stool, surgical bed, patient height, patent head rotation and angle, surgical instrument values and any or all other controllable parameters is greatly reduced, reducing the turnaround time between surgical procedures, and increasing operating theater efficiency. Specifically, an increased number of surgical procedures may be performed in a given operating room or theatre in a given period of time than was previously achievable. Thus the system and method of the invention is an advancement and improvement of the state of the art of operating room efficiency.

In embodiments, floor mat 107 may be of sufficient dimension that the wheels or supports of surgical bed 002 or surgeon stool 003, or both, rest upon it. Floor mat 107 may comprise markings for locating the wheels or supports of surgical bed 002 or surgeon stool 003, or both, as well as one or more foot controls for operating surgical equipment. Thus, the relationship between the location of surgical bed and foot controls may be controlled to surgeon preference.

In any of the embodiments, surgical bed 002 may comprise memory foam. "Memory foam" as used herein includes within its meaning "viscoelastic" polyurethane foam or low-resilience polyurethane foam (LRPu) that has an open-cell solid structure that matches pressure against it, yet slowly springs back to its original shape. In embodiments, exemplary memory foam material is characterized by a density in a range between less than 1.0 lb/ft³ to 8 lb/ft³.

In embodiments, the system of the invention may comprise measuring device 103, angle measuring device 125, adjustable surgeon handrest 205 that is adjustable for position and orientation, and headrest 101. In embodiments, the system of the invention may also comprise neck rest 102. In embodiments, the system of the invention may also comprise floor mat 107. Further, the system and method of the invention may comprise at least one local computer 1000 in data communication, either wired or wirelessly, with controllable actuators or other adjusting devices, such as controllable pumps for inflating or deflating inflatable bladders comprising headrest 101, surgical bed 102, surgeon stool 103, and with surgical equipment, for controlling the controllable parameters of each of these elements. In any of the embodiments, any of the above features and elements may be present in any quantity and in any combination.

In embodiments, each of the adjustments described herein as being controllable or adjustable may be controlled by the entry of parameters by a user into either a mobile electronic device 1005, such as, for example, a smart phone or tablet that is in communication with local computer 1000, or directly into local computer 1000, whereupon controller 1001 may operate to command any or all of the controllable actuators, pumps, surgical equipment, or other controllable devices to adjust themselves to a desired parameter value for each controllable devices. Thus, by entry of only one, or just a few, commands, each controllable device in the operating theatre may be commanded to adjust themselves to a specific surgeon's predetermined preferences. The system of the invention eliminates surgical equipment setup time and error, improves surgical equipment setup accuracy, improves surgical equipment setup repeatability, and reduces operating theatre setup time over the systems and methods of the prior art. Operating room efficiency is improved due to reduced setup time between surgical procedures, allowing higher throughput of patents in a given period of time. Patient outcomes are improved due to reduced surgeon fatigue.

In embodiments, the invention may comprise a method for reducing the physiologic strain on a surgeon and for reducing turn-around time between patient surgical procedures, wherein the surgical procedures are performed successively on patients who are each disposed upon a surgical bed 002, by providing the ability to repeatably locate and orient surgical assistive features and patient body portions such that a surgeon is presented with similar location and orientation of surgical assistive features and patient body portions from one surgical procedure to the next, comprising: providing a system comprising a headrest 101 for supporting a patient's head during surgery, wherein a height J of the headrest above a reference point of the surgical bed is adjustable by adjusting the patient's head height to a pre-determined height J above the reference point 004 of the surgical bed 002, by adjusting the height of the headrest for example, inflating or deflating inflatable bladders comprising head rest 101; adjusting the patient's head rotation by rotating the patient's head while the patient's head is disposed upon the headrest until the rotation of the patient's head reaches a desired rotation a as measured relative to vertical reference (or normal) line 140; adjusting a height of the surgical bed 002 until the surgical bed height reaches a desired height G above a reference point such as a floor upon which the surgical bed is disposed 122 as measured by the height measuring instrument 103 and surgical bed marker or laser 105; adjusting a height of a surgeon wrist rest to a desired height above a patient's corneal apex; and adjusting a height of a stool until the stool sitting surface reaches a desired height C above the floor 122 upon which the sitting stool is disposed as measured by the height measuring instrument 103 and marker or laser 106.

In embodiments, the method of the invention may comprise the steps of adjusting the patient's head height to a pre-determined height J above the reference point 004 of the surgical bed by adjusting the height of the headrest; adjusting the patient's head rotation by rotating said patient's head, while the patient's head is disposed upon the headrest, until the rotation of the patient's head reaches a desired rotation a as measured relative to a vertical reference (or normal) line 140; adjusting a height of the surgical bed until the surgical bed height reaches a desired height from the second reference point as measured by the surgical bed height measuring instrument; adjusting a height of a surgeon wrist rest to a desired height above a patient's corneal apex; and adjusting a height of a stool until the stool sitting surface reaches a desired height from said second reference point as measured by the stool height measuring instrument; where the steps of the method are carried out by controllable actuators or fluid pumps that are in communication with a controller, and wherein the controller has received user input commands establishing the parameters for control of one or more of the controllable actuators or fluid pumps.

In embodiments, the system, apparatus and method of the invention may be utilized as follows. A surgeon may pre-determine, based upon personal preference and experience, one or more of the following parameters for positioning and orienting surgical assistive features, apparatuses, equipment and portions of a patients body preferred by the surgeon for surgical procedures: height of surgical bed from floor G, height of stool sitting surface from floor C, height of portion of patient's body (such as for example, corneal apex) from floor E, distance from of portion of patient's body (such as for example, corneal apex) from patient resting surface of surgical bed J, angle of rotation of patient's head α, angle of headrest γ, location of surgical equipment foot pedals on the floor 122, location of surgical bed wheels on floor, location of lighting stand(s) on floor, location of microscope, and location of other surgical equipment. The height of surgical bed from floor G, height of stool sitting surface from floor C, height of portion of patient's body (such as for example, corneal apex) from floor E, distance from of portion of patient's body (such as for example, corneal apex) from patient resting surface of surgical bed J, angle of rotation of patient's head α, angle of headrest γ may be recorded in an operating theater notebook or other media for latter retrieval and use, or maybe entered into controller 1001 of computer 100 via an input device such a keyboard or touchscreen that are in communication with controller 1001 and stored in storage media 1002 for later retrieval and use. The desired location of surgical equipment foot pedals on the floor 122, location of surgical bed wheels on floor, location of lighting stand(s) on floor, location of microscope, and location of other surgical equipment may be marked on a mat 107, the markings locating the position and orientation of these items. Each surgeon in a group of surgeons may have their own mat, or, alternatively, a single mat may be used to store the location markings of such equipment for a plurality of surgeons.

Prior to the surgeon entering the surgical theater, operating room personal may adjust one or more of the height of surgical bed from floor G, height of stool sitting surface from floor C, height of portion of patient's body (such as for example, corneal apex) from floor E, distance from of portion of patient's body (such as for example, corneal apex) from patient resting surface of surgical bed J, angle of rotation of patient's head α, angle of headrest γ for a particular surgeon who is schedule to utilized the operating theater by referring to the operating theater notebook or other media to retrieve the particular surgeon's desired settings for these measurements, and, using the height measure tool 103 and adjustments of the operating room apparatus' as hereinbefore described, adjust the height of surgical bed from floor G, height of stool sitting surface from floor C, height of portion of patient's body (such as for example, corneal apex) from floor E, distance from of portion of patient's body (such as for example, corneal apex) from patient resting surface of surgical bed J, angle of rotation of patient's head α, angle of headrest γ to the predetermined settings for the particular surgeon. In this way, the operating theater personnel may manually cause these adjustments to be made to the operating theater apparatuses and equipment, making the apparatuses and equipment ready for use by the surgeon when the surgeon enters the operating theater.

Alternatively, in an electronic embodiment of the invention, the height of surgical bed from floor G, height of stool sitting surface from floor C, height of portion of patient's body (such as for example, corneal apex) from floor E, distance from of portion of patient's body (such as for example, corneal apex) from patient resting surface of surgical bed J, angle of rotation of patient's head α, and angle of headrest γ may be adjusted by controller 1001 by operating theater personnel entering the particular surgeon's name or other identifying indicia into controller 1001, via keyboard, touchscreen, or other input device in communication with controller 1001. A computer program, or application, in the form of non-transitory computer readable and executable instructions may then be executed by controller 1001, which may be in communication with pumps, rotary motors, actuators or encoders, to cause these elements to adjust one or more of the height of surgical bed from floor G, height of stool sitting surface from floor C, height of portion of patient's body (such as for example, corneal apex) from floor E, distance from of portion of patient's body (such as for example, corneal apex) from patient resting surface of surgical bed J, angle of rotation of patient's head α, angle of headrest γ to the predetermined values established by that particular surgeon. These values maybe stored in media 1002 for retrieval and use by controller 1001. Thus, in the case in which one or more of the height of surgical bed from floor G, height of stool sitting surface from floor C, height of portion of patient's body (such as for example, corneal apex) from floor E, distance from of portion of patient's body (such as for example, corneal apex) from patient resting surface of surgical bed J, angle of rotation of patient's head α, angle of headrest γ are controlled and adjusted by controller 1001 upon command from operating theater personnel, controller 1001 may command the pumps, rotary motors, actuators or encoders of the invention to be actuated to these predetermined parameters. In this way, the entry of a command into controller 1001 will cause these adjustments to be made to the operating theater apparatuses and equipment, making the apparatuses and equipment ready for use by the surgeon when the surgeon enters the operating theater.

A surgeon may also predetermine desired locations and orientations of the surgical sitting stool, surgical bed, one or more surgical equipment foot pedals, one or more lighting apparatus, and other equipment that is disposed on the floor in the operating theater. These locations may be marked on the floor surface, or alternatively on a mat or other floor surface covering, that lies under the operating theatre equipment. The markings may indicate locations for the surgical sitting stool, surgical bed, one or more surgical equipment foot pedals, one or more lighting apparatus, and other equipment that is disposed on the floor in the operating theater. Prior to the surgeon entering the operating theater, the operating theater personnel may locate the surgical sitting stool, surgical bed, one or more surgical equipment foot pedals, one or more lighting apparatus, and other equipment on the floor or mat, using the markings to identify the predetermined position and orientation of the surgical sitting stool, surgical bed, one or more surgical equipment foot pedals, one or more lighting apparatus, and other equipment. Thus, when the surgeon enters the operating theater, the surgical sitting stool, surgical bed, one or more surgical equipment foot pedals, one or more lighting apparatus, and other equipment are located in the desired predetermined position and orientation.

It can be seen and appreciated that the use of the system, apparatus', and method of the invention greatly reduce time lost rearranging equipment and positioning patient body parts and surgical assistive equipment by the surgeon, allowing increased effective use of time, increasing patient throughput, reducing surgeon fatigue, and enabling improved medical outcomes.

The method steps of the invention may be carried out in any order, and, in embodiments, the method of the invention may not necessarily comprise every step described herein. It is to be understood that the embodiments of the system and method of the invention described herein are exemplary only and that the scope of the intended invention as set forth in the written description, drawings and claims includes all alternate embodiments and legal equivalents thereof.

What is claimed is:

1. A system for reducing the physiologic strain on a surgeon and for reducing turn around time between patient surgical procedures, wherein said surgical procedures are performed successively on patients who are each disposed upon a surgical bed, by providing the ability to repeatably locate and orient surgical assistive features and patient body portions such that surgeon is presented with similar location of surgical assistive features and patient body portions from one surgical procedure to the next, comprising:

one or more headrests for supporting a patient's head;

one or more rests for supporting a patient's neck;

an angle measuring device for measuring the rotation of a patient's head;

an eye height measuring device for measuring the height of the patient's eye from a first reference point;

a surgical bed height measuring instrument for measuring the height of a reference point of the surgical bed from a second reference point;

a stool height measuring instrument for measuring the height of a sitting surface of a surgeon stool for the surgeon to use during surgical procedures from said second reference point;

an adjustable wrist rest; and a head height measuring instrument for measuring a height of a reference point of a patient's head from said second reference point.

2. The system of claim 1, wherein said headrest comprises one or more inflatable bladders for supporting a patient's head, and wherein the height of said patient's head from said second reference point may be adjusted up or down by inflating or deflating said one or more inflatable bladders.

3. The system of claim 2, wherein said one or more bladders are pneumatically inflatable.

4. The system of claim 3, wherein said one or more bladders are in fluid communication with an air pump for inflating said one or more bladders.

5. The system of claim 4, wherein each of said air pumps are controllable and are in communication with a local computer for controlling the inflation and deflation of said bladders.

6. The system of claim 5, wherein said local computer is in communication with one or more mobile devices, electronic devices, or computers, and wherein said one or more mobile devices, electronic devices, or computers are adapted to receive user input, said user input defining parameters for controlling said air pumps or said actuators, or both, to adjust to a specific value.

7. The system of claim 6, wherein said specific values are determined by surgeon preference.

8. The system of claim 4, wherein said air pump is manually operated.

9. The system of claim 2, wherein said one or more inflatable bladders is in fluid communication with a valve adapted to allow a fluid within the one or more inflatable bladders to escape, thus deflating the one or more inflatable bladders.

10. The system of claim 1, wherein said surgical bed height measuring instrument, said stool height measuring instrument, and said head height measuring instrument are the same instrument, comprising movable markers for indicating a distance from said second reference point to a reference point of said surgical bed, the sitting surface of said stool, and a reference point of a patient's head, respectively.

11. The system of claim 1, wherein said second reference point is a floor of an operating room, and wherein said first reference point is a resting surface of a surgical bed.

12. The system of claim 1, wherein said surgical bed height measuring instrument, said stool height measuring instrument, and said head height measuring instrument each further comprise movable markers for indicating a distance from said second reference point to a reference point of said surgical bed, the sitting surface of said stool, and a reference point of a patient's head, respectively.

13. The system of claim 1, further comprising an angle measuring device for measuring the rotation of a patient's head relative to normal or relative to the resting surface of a surgical bed.

14. The system of claim 1, further comprising a floor mat for locating at least one surgical instrument foot pedal control, wherein a location of said at least one surgical instrument foot pedal control is determined by surgeon preference.

15. The system of claim 1, wherein said surgical bed, said surgeon stool, and said wrist rest each comprise controllable actuators for adjusting their height relative to a reference point, and each of said controllable actuators are in communication with a local computer for controlling their height.

16. A method for reducing the physiologic strain on a surgeon and for reducing turn around time between patient surgical procedures, wherein said surgical procedures are performed successively on patients who are each disposed upon a surgical bed, by providing the ability to repeatably locate and orient surgical assistive features and patient body portions such that a surgeon is presented with similar location and orientation of surgical assistive features and patient body portions from one surgical procedure to the next, comprising:
provisioning a system comprising a headrest for supporting a patient's head during surgery, wherein a height of said headrest above a reference point of the surgical bed is adjustable;
adjusting said patient's head height to a pre-determined height above the reference point of the surgical bed by adjusting the height of the headrest;
adjusting said patient's head rotation by rotating said patient's head while said patient's head is disposed upon the headrest until the rotation of said patient's head reaches a desired rotation as measured relative to normal;
adjusting a height of said surgical bed until said surgical bed height reaches a desired height from a second reference point as measured by said surgical bed height measuring instrument;
adjusting a height of a surgeon wrist rest to a desired height above a patient's corneal apex; and
adjusting a height of a stool until said stool sitting surface reaches a desired height from said second reference point as measured by said stool height measuring instrument.

17. The method of claim 16, wherein said headrest comprises one or more inflatable bladders for supporting a patient's head, and wherein the height of said patient's head from said reference point may be adjusted up or down by inflating or deflating said one or more inflatable bladders.

18. The method of claim 17, wherein said one or more bladders are pneumatically inflatable.

19. The method of claim 18, wherein said one or more bladders are in fluid communication with an air pump for inflating said one or more bladders.

20. The method of claim 19, wherein said air pump is manually operated.

21. The method of claim 17, wherein said one or more inflatable bladders is in fluid communication with a valve adapted to allow a fluid within the one or more inflatable bladders to escape, thus deflating the one or more inflatable bladders.

22. The method of claim 17, further comprising the step of placing a floor mat in a desired location on the floor, wherein the floor has marking for locating at least one surgical instrument foot pedal control, wherein the location of the at least one surgical instrument foot pedal control is determined by surgeon preference.

23. The method of claim 16, wherein the steps of:
adjusting said patient's head height to a pre-determined height above the reference point of the surgical bed by adjusting the height of the headrest;
adjusting said patient's head rotation by rotating said patient's head while said patient's head is disposed upon the headrest until the rotation of said patient's head reaches a desired rotation as measured relative to normal;
adjusting a height of said surgical bed until said surgical bed height reaches a desired height from said second reference point as measured by said surgical bed height measuring instrument;
adjusting a height of a surgeon wrist rest to a desired height above a patient's corneal apex; and
adjusting a height of a stool until said stool sitting surface reaches a desired height from said second reference point as measured by said stool height measuring instrument;

where the steps of the method are carried out by controllable actuators or fluid pumps that are in communication with a local computer, and wherein said local computer has received user input commands establishing the parameters for control of each of the controllable actuators or fluid pumps.

* * * * *